US010857193B2

(12) United States Patent
Pischel et al.

(10) Patent No.: US 10,857,193 B2
(45) Date of Patent: Dec. 8, 2020

(54) EXTRACT FORMULATION OF *OPUNTIA FICUS INDICA*

(75) Inventors: Ivo Pischel, Rossbach (DE); Bjoern Feistel, Andernach (DE); Bernd Walbroel, Konigswinter (DE)

(73) Assignee: FINZELBERG GMBH & CO. KG, Andernach (DE)

( * ) Notice: Subject to any disclaimer, the term of this patent is extended or adjusted under 35 U.S.C. 154(b) by 0 days.

(21) Appl. No.: 12/741,562

(22) PCT Filed: Nov. 6, 2008

(86) PCT No.: PCT/EP2008/065048
§ 371 (c)(1),
(2), (4) Date: Aug. 23, 2010

(87) PCT Pub. No.: WO2009/060024
PCT Pub. Date: May 14, 2009

(65) Prior Publication Data
US 2010/0323045 A1 Dec. 23, 2010

Related U.S. Application Data

(60) Provisional application No. 61/002,058, filed on Nov. 6, 2007.

(30) Foreign Application Priority Data

Nov. 6, 2007 (EP) .................................... 07120081

(51) Int. Cl.
*A61K 36/33* (2006.01)

(52) U.S. Cl.
CPC .................... *A61K 36/33* (2013.01)

(58) Field of Classification Search
CPC ...................................................... A61K 36/33
See application file for complete search history.

(56) References Cited

U.S. PATENT DOCUMENTS

| 2,082,952 | A | 6/1937 | Gruwell et al. |
| 3,860,710 | A | 1/1975 | Giovannozzi-Sermanni et al. |
| 6,447,820 | B1 * | 9/2002 | Niazi ............................ 424/767 |
| 6,576,286 | B1 * | 6/2003 | Chen ............................ 426/599 |

FOREIGN PATENT DOCUMENTS

| DE | 10350194 A1 | 6/2005 | |
| EP | 1679009 A1 * | 7/2006 | ............. A23L 33/22 |
| KR | 20020092021 A | 12/2002 | |
| KR | 20030023398 A | 3/2003 | |
| KR | 20030035974 A | 5/2003 | |
| KR | 2004091969 A * | 11/2004 | |
| KR | 1020040091969 B1 | 11/2004 | |
| KR | 1020040094173 A | 11/2004 | |
| KR | 2006117645 A * | 11/2006 | |
| KR | 1020060117645 B1 | 11/2006 | |

OTHER PUBLICATIONS

Hamdi. Bioprocess Engineering 17 (1997) 387-391.*
Galati et al.; "*Opuntia ficus indica* (L.) Mill. Mucilages Show Cytoprotective Effect on Gastric Mucosa in Rat"; Phytotherapy Research; Apr. 4, 2007; pp. 344-346.
Wolfram et al.; "Effect of Prickly Pear (*Opuntia robusta*) on Glucose-and Lipid-Metabolism in Non-Diabetics with Hyperlipidemia—A Plot Study"; Wiener Klinische Wochenschrift; 2002; pp. 840-846.
Wolfram et al; "Effect of Prickly Pear (*Opuntia robusta*) on Glucose- and lipid-Metabolism in Non-Diabetics with Hyperlipidemia—A Pilot Study"; Springer-Verlag 2002; pp. 840-846.
Shin et al; "Hypoglycemic Activity of *Opuntia ficus-indica* var. Sabotan on Alloxan-or Streptozotocin-Induced Diabetic Mice"; Korean Journal of Pharmacognosy vol. 34(1); 2003; pp. 75-79.
Park et al; "Studies on the Pharmacological Actions of Cactus: Identification of It's Anit-Inflammatory Effect"; Arch. Pharm. Res vol. 21; 1998; 30-34.
Marles et al; "Antidiabetic Plants and Their Active Constituents"; Phytomedicine vol. 2; 1995; 137-189.
Galati et al; "*Opuntia ficus indicia* (L.) Mill. Mucilages Show Cytoprotective Effect on Gastric Mucosa in Rat"; Phytotherapy Research. 21; 2007; pp. 344-346.
Kossori et al; Compostion of Pulp, Skin and Seeds of Prickly Pears Fruit (*Opuntia ficus indica* sp.); Plant Foods for Human Nutrition 52.; 1998; pp. 263-270.
German Office Action dated Jan. 24, 2013 for German application No. 11 2008 002 948.2.
English translation of International Preliminary Report on Patentability dated May 11, 2010 in corresponding International Application No. PCT/EP2008/065048.
English translation of Written Opinion of the International Search Authority dated May 6, 2010 in corresponding International Application No. PCT/EP2008/065048.
English translation of International Search Report dated May 14, 2009 in corresponding International Application No. PCT/EP2008/065048.
Stintzing et al; "Cactus Stems (*Opuntia* spp): A Review on their Chemistry, Technology, and Uses"; Mol. Nutr. Food Res. 2005, 49; pp. 175-194.
Tesoriere et al; "Health Benefits and Bioactive Components of the Fruits from *Opuntia ficus-indica*".; J. PACD 2006; pp. 73-90.
Frati et al; "Hypoglycemic Effect of Opuntia Streptacantha"; Arch Invest Med (Mex.),1991; pp. 333-336.
Trejo-Gonzalez et al; "A Purified Extract from Prickly Pear Cactus (*Opuntia fuliginosa*) Controls Experimentally Induced Diabetes in Rats"; Journal of Ethnopharmacology, 1996; pp. 27-33.

(Continued)

Primary Examiner — Amy L Clark
(74) Attorney, Agent, or Firm — Ohlandt, Greeley, Ruggiero and Perle, LLP

(57) ABSTRACT

Cactus pear (*Opuntia*) extract compositions, their methods of preparation, and their uses in products are provided. The *Opuntia* extract compositions are a mixture of an extract prepared by extraction of *Opuntia* fruit/fruit parts, combined with an extract prepared by extraction of *Opuntia* cladodes/cladode parts. The resulting *Opuntia* extract compositions exhibit improved therapeutic characteristics as compared with known *Opuntia* fruit juices or extracts, including increased hypoglycemic effects.

9 Claims, 2 Drawing Sheets

(56) References Cited

OTHER PUBLICATIONS

Opuntia Humifusa; http'//en.wikipedia.org/wiki/Opuntia humifusa; May 22, 2013; pp. 1-2.
Opuntia Ficus-Indica; http'//en.wikipedia.org/wiki/Opuntia ficus-indica; May 22, 2013; pp. 1-5.
Mosshammer et al; "Cactus Pear Fruits (*Opuntia* spp.): A Review of Processing Technologies and Current Uses"; 2006 J. PACD; pp. 1-25.
Hansel et al; "Pharmakognosie—Phytopharmazie"; Dec. 12, 2007; pp. 1-10.
Goycoolea et al; "Pectins from *Opuntia* spp: A Short Review"; J. PACD; Feb. 19, 2003; pp. 1-14.
Subash et al; "Cinnamaldehyde—A Potential Antidiabetic Agent"; ScienceDirect 2007; Jul. 12, 2006; pp. 15-22.
Verspohl et al; "Antidiabetic Effect of Cinnamomum Cassia and Cinnamomum Zeylanicum In Vivo and In Vitro"; Phytother. Res 19 (2005); pp. 203-206.
Butterweck et al.; "Comparative Evaluation of Two Different Opuntia ficus-indica Extracts for Blood Sugar Lowering Effects in Rats"; Phytotherapy Research; Phytother. Res. (2010) John Wiley & Sons, Ltd., 6 pages.
J.S. Peterson; *Opuntia ficus-indica* (L.) Mill. Barbary fig; Mar. 13, 2002; http://www.plants.usda.gov/core/profile?symbol=OPFI.
Bodner et al.; *Opuntia humifusa* (Raf.) Raf. devil's-tongue; Jun. 13, 2002; http://plants.usda.gov/core/profile?symbol=OPHU.
Definition of "Drug Extract Ratio (DER)"; European Medicines Agency, Post-authorisation Evaluation of Medicines for Human Use, London, Jan. 29, 2009, EMEA/HMPC/CHMP/CVMP/2875339/2005 Rev. 1, p. 15/19.

\* cited by examiner

EXTRACT FORMULATION OF *OPUNTIA FICUS INDICA*

CROSS-REFERENCE TO RELATED APPLICATIONS

This application is related, and claims priority, to European application Serial No. 07120081.0, filed on Nov. 6, 2007, PCT application No. PCT/EP2008/065048 filed on Nov. 6, 2008 and Provisional application Ser. No. 61/002,058 filed on Nov. 6, 2007, under 35 U.S.C. § 119 and 35 U.S.C. § 365.

BACKGROUND

1. Field of the Disclosure

This disclosure relates to cactus pear extract formulations, methods for their manufacture and their use. Cactus pear extract formulations have a positive effect on blood glucose levels and can be used for the treatment and prevention of diabetes mellitus II.

2. Discussion of the Background Art

The cactus pear (*Opuntia* spp., *Opuntia ficus indica*) has for centuries been used in traditional medicine in the New World, in South, Central and North America, and also in the countries of the Mediterranean, North Africa and other areas for treating illnesses, for alleviating symptoms and for preventing metabolic disorders.

Stintzing F C and Carle R (Cactus stems (*Opuntia* spp.) A review on their chemistry, technology, and uses. Mol. Nutr. Food Res. 2005, 49, 175-194) describe a range of uses of cactus stems (cladodes), including anti-oxidant, anti-inflammatory (including in ulcers), analgesic, hypoglycaemic, anti-diabetic and blood lipid and cholesterol lowering effects. Due to the pigmented betalain derivatives they contain, cactus pears, the edible fruit of *Opuntia* species, have been described as having uses as food-stuffs, in particular as food colouring concentrates, and as therapeutic remedies. A review by Livrea M A and Tesoriere L (Health Benefit and Bioactive Components of the Fruits from *Opuntia ficus-indica*. J. PACD 2006, 73-90) showed, in particular in the use of the edible parts of the fruit and fruit juice, anti-oxidant activity, cardio-protective, anti-ulcer and hepato-protective effects, as well as a protective effect on nervous tissue and cancer prophylaxis. Antioxidant betalain derivatives with free radical scavenging properties are cited as the bioactive substances.

Traditional use of *Opuntia* in type 2 diabetes mellitus is limited to the use of fresh cladodes (young cactus shoots), which are generally boiled, fried or grilled and eaten in quantities of up to 500 grams (Frati A C, Xilotl Díaz N, Altamirano P, Ariza R, López-Ledesma R.; The effect of two sequential doses of *Opuntia streptacantha* upon glycemia. Arch Invest Med (Mex.), 1991, 333-6).

In 1933 Gruwell C E and Preene H E described an antidiabetic activity for an extract of fleshy branches of *Opuntia phaeacantha* (U.S. Pat. No. 2,082,952). Neither active components nor purification steps had been mentioned. They disclosed the use of intense solar radiated plants as a need for effective and active products.

Even in relatively high dosages, dried, powdered cladodes in pharmaceutical forms of administration such as tablets and capsules have a blood lipid reducing effect only and are marketed solely for this purpose (www.neopuntia.com).

Undefined cladode extracts produced using organic solvents have been described in the literature as having a hypoglycaemic effect. (Trejo-Gonzalez A et al. A purified extract from prickly pear cactus (*Opuntia fuliginosa*) controls experimentally induced diabetes in rats. Journal of Ethnopharmacology, 1996, 27-33.)

Galati E M et al. (*Opuntia ficus indica* (L.) Mill. mucilages show cytoprotective effect on gastric mucosa in rat), Phytotherapy Research 21 (2007), 344-346 described an aqueous extraction of fresh cladodes, followed by a reprecipitation of the extract in ethanol to receive a small pectin-fraction and a mucilage fraction (each about 10%). A gastroprotective effect of the mucilage extract is described. No relation to a glucose- or lipid-metabolic activity is described.

Other than the applications described above, the literature, including patent literature, describes the use of plant extracts from cladodes of prickly pears for alcohol-induced hangovers (KR 2004-0094173), as a neuroprotective agent (KR 2003-0035974), as an immune stimulant (KR 2002-0092021), for dermatological problems (JP 2002-0072130; KR 2003-0023398) and as a microbicide (U.S. Pat. No. 3,860,710; KR 2003-0023398). The fruits (cactus pears) are extracted and concentrated to obtain food colourings (beta-lain, etc.) (KR 2003-0035974; Moβhammer M R, Stintzing F C, Carle R. Cactus Pear Fruits (*Opuntia* spp.): A Review of Processing Technologies and Current Uses. 2006, J. PACD, 1-25).

DE 103 50 194 discloses the plant's flowers as an extracted plant component which is neither cladode nor fruit. The ethanolic flower extract is reputed to be neuroprotective.

Wolfram R M et al. (Effect of prickly pear (*Opuntia robusta*) on glucose- and lipid-metabolism in non-diabetics with hyperlipidemia—A pilot study), Wiener klinische Wochenschrift 114 (2002), 804-846 describe pectin as the mode of action of metabolic activity from fruit pulp and stated an insulin-lowering side-effect after administration of about 250 g fruits per day.

No synergistic anti-diabetic or hypoglycaemic activity has previously been ascribed to any combination of fruits, fruit juice or fruit components with cladodes or any extracts thereof.

The object and purpose of the present disclosure is to reproducibly manufacture cactus pear extract preparations with improved characteristics, in particular an increased hypoglycaemic effect.

Further, it makes use of novel, inexpensive plant components which are readily available and thus previously unused raw materials.

SUMMARY

Surprisingly, it was found that this object can be achieved using a method for manufacturing cactus pear extract preparation encompassing the steps a)—extracting plant parts selected from fruit, fruit parts, and mixtures thereof using an extractant containing water and from 0 to 70% by weight of alcohols;
at least partially removing the extractant;

b)—extracting plant parts selected from cladodes, cladode parts and mixtures thereof using an extractant containing water and from 0 to 70% by weight of alcohols;
at least partially removing the extractant;

c)—mixing together the extracts of step a) and b).

The fruits, fruit parts, cladodes and cladodes parts are plant parts from *Opuntia*.

In one embodiment the method encompasses
1. extraction from raw materials a) fresh or dried fruit skin (pomace or fruit residue following juice extraction) and/or fresh or dried cladodes or the residue of same following pressing, b) mixing the raw material with a hydroalcoholic extraction medium in order to obtain a raw extract, where the hydroalcoholic extraction medium contains 0 to 70% vol alcohol;
2. at least partial removal of the alcoholic component of the raw extract in order to obtain a concentrated, primarily aqueous or almost water-free thick extract;

The extract preparation obtained may be processed:
a) immediately for the manufacture of liquid formulations (syrups, drops, drinks);
b) for filling soft gelatine capsules or
c) with or without carriers to dried extracts.

In one embodiment, instead of an extract from fruits or fruit parts, juice from fruits of Opuntia is mixed with an extract from cladodes, cladode parts or mixtures thereof.

One object of the disclosure is the conversion of the extracts in dried cactus pear extract preparations with standard pharmaceutical adjuvants into various pharmaceutical forms of administration.

Plant components from plants selected from the Cactaceae family, especially from the Opuntioideae sub-family, especially from the Opuntieae tribe and especially one of the species *Opuntia acanthocarp* Engelmann & Bigelov, *Opuntia aciculata* Griffiths, *Opuntia albicans* Salm-Dyck, *Opuntia anacantha* Speg., *Opuntia arcei* Cardenas, *Opuntia aurantiaca* Lindl., *Opuntia azurea* Rose, *Opuntia bahiensis* Br. & Rose, *Opuntia basilaris*: Engelmann & Bigelov, *Opuntia berteri* (Colla) Ritter, *Opuntia bigelowii* Engelmann, *Opuntia bispinosa* Backeberg, *Opuntia boliviana*, *Opuntia bonplandii* (Kunth), *Opuntia cardiosperma* K. Schum., *Opuntia chaffeyi* Br. & Rose, *Opuntia chlorotica* Engelm. & J. M. Bigelow, *Opuntia cochenillifera* (L.) Mill., *Opuntia crassa* Haw., *Opuntia curassavica* (L.) Mill., *Opuntia decumbens* Salm-Dyck, *Opuntia dejecta* Salm-Dyck, *Opuntia delaetiana* (F. A. C. Weber) Vaupel, *Opuntia echios* J. T. Howell, *Opuntia elata* Link & Otto ex Salm-Dyck, *Opuntia elatior* Mill., *Opuntia eilisiana* Griffiths, *Opuntia engelmannii* Salm-Dyck ex Engelm., *Opuntia ficus-indica* (L.) Mill., *Opuntia fragilis* (Nutt.) Haw., *Opuntia gosseliniana* F. A. C. Weber, *Opuntia hyptiacantha* F. A. C. Weber, *Opuntia karwinskiana* Salm-Dyck, *Opuntia lanceolate* (Haw.) Haw., *Opuntia larreyi* F. A. C. Weber ex J. M. Coult. *Opuntia leucotricha* DC., *Opuntia macrocentra* Engelm., *Opuntia macrorhiza* Engelm., *Opuntia megasperma* J. T. Howell, *Opuntia microdasys* (Lehm.) Pfeiff., *Opuntia mieckleyi* K. Schum., *Opuntia monacantha* Haw., *Opuntia phaeacantha* Engelm., *Opuntia pilifera* F. A. C. Weber, *Opuntia polyacantha* Haw., *Opuntia pottsii* Salm-Dyck, *Opuntia puberula* Pfeiff-, *Opuntia quitensis* F. A. C. Weber, *Opuntia rastrera* F. A. C. Weber, *Opuntia repens* Bello, *Opuntia robusta* H. L. Wendl. ex Pfeiff., *Opuntia salmiana* J. Parm. ex Pfeiff., *Opuntia santa-rita, Opuntia scheeri* F. A. C. Weber, *Opuntia schlckendantzii* F. A. C. Weber, *Opuntia schumannii* F. A. C. Weber ex A. Berger, *Opuntia spinullfera* Salm-Dyck, *Opuntia stenopetala* Engelm., *Opuntia streptacantha* Lern., *Opuntia stricta* (Haw.) Haw., *Opuntia sulphurea* Gillies ex Salm-Dyck, *Opuntia tomentosa* Salm-Dyck, *Opuntia triacanthos* (Willd.) Sweet, *Opuntia tuna* (L.) Mill. (Syn.: *Cactus tuna* L.), *Opuntia undulata* Griffiths, *Opuntia xvaseyi* (J. M. Coult.) Britton & Rose, *Opuntia velutina* F. A. C. Weber, and hybrids of these species are altogether demotic described as "prickly pear", however especially *Opuntia ficus indica* (L.) Mill. is suitable as starting material for the inventive formulation of "cactus pear" extracts.

DETAILED DESCRIPTION OF THE PREFERRED EMBODIMENT

Figure 1:
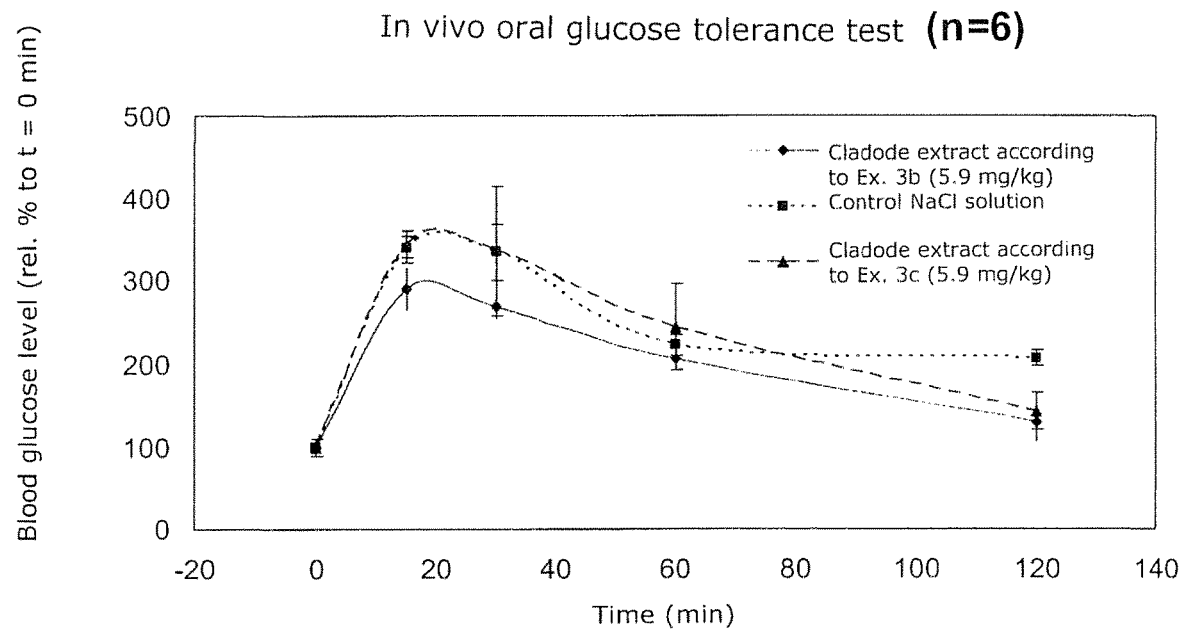
FIG. 1 shows the in vivo oral glucose tolerance test following administration

According to the inventive method, individual cactus pear raw materials or a mixture thereof are first extracted using a hydroalcoholic extraction medium or pure water. The plant material is usually chopped into small pieces (8-12 mm) to speed up and increase the efficiency of extraction. A suitable ratio of plant material to extraction medium is between 1:5 and 1:30 by weight, preferably 1:10 to 1:20.

Persons skilled in the art will be aware that extraction can be improved by heating the extraction medium. Suitable temperatures for the extraction process range from room temperature to about 100° C., preferably in the range 50 to 90° C.

Typical extraction times range from 1 to 12 hours, preferably 2 to 6 hours.

In contrast to prior art methods, in which alcohol-water mixtures with a high alcohol concentration or even non-alcohol organic solvents are used, the extraction process is carried out using an extraction medium which preferably contains a low amount of or no alcohol. The alcohol concentration ranges from 0 to 70 vol.-% of the extraction medium, preferably between 0 and 20 vol.-%, more preferably between 0 and 10 vol.-%. Suitable alcohols include in particular ethanol, but also methanol, isopropanol, polyhydric alcohols and mixtures thereof.

The anti-diabetic properties of a leaf extract of *Opuntia ficus indica* ssp. in water and in EtOH 70% v/v are described in examples 1a and 1b. Both extracts show a hypoglycaemic effect. Further, release of endogenous insulin is significantly stimulated. The aqueous extract is superior to the hydroalcoholic extract (EtOH 70% v/v) in this respect.

After extraction, the extraction medium is separated from the plant residue. Suitable methods for doing so include decanting, filtration, centrifugal separation, etc.

The alcohol component, for example, of the raw extract obtained in this manner is then partly or completely removed. This can be carried out using a bubble or plate evaporator, for example. By adding further water, the alcohol content can be reduced to, for example, <2% w/w. The resulting percentage of dry matter ranges from 40 to 70% (m/m). The aqueous extract thus obtained is hereafter referred to as thick extract.

Further steps for separating and purifying inactive/active components can be applied to extracts or thick extracts obtained using the inventive method at any concentration.

The following variants of the separation and purification process can be used to increase efficacy by releasing active principles and substances:

High-molecular weight, biologically poorly active and poorly soluble substances which have been extracted together with the primary extract can be broken down or removed using enzyme treatment (pectinases, etc.), membrane filtration or autoclaving, so that the soluble bioactive substances are enriched and the remaining "post-processed, purified extract" possesses a higher efficacy.

Following the separation and purification process, a cactus pear extract which can be further processed by persons skilled in the art in the usual manner is obtained. By preference the extract is dried. This can be carried out by, for example, lyophilisation (freeze-drying), spray-drying, vacuum-drying, etc. By preference, adjuvants are used for drying in order to obtain a free-flowing dry extract. Drying adjuvants which can be used include maltodextrin, mono-, di- and oligosaccharides (sugars), protein mixtures and hydrolysed protein mixtures including hydrolysed collagen, celluloses and cellulose derivatives, starches, starch derivatives and modified starches as well as adjuvants of particular suitability for diabetics such as microcrystalline celluloses (MCC), polyvinylpyrrolidone (PVP), gum arabic or fructose. Gentle drying processes such as vacuum-drying, freeze-drying or spray-drying with product temperatures less than 55° C. are preferred.

The object of the disclosure is also a galenic cactus pear extract preparation obtained using the method of the disclosure, which can be used for the direct manufacture of a wide range of pharmaceutical forms of administration.

Surprisingly, the inventive cactus pear extract preparations contained relatively small amounts of sterols (<100 ppm) and in particular relatively small amounts of beta-sitosterol (<10 ppm)—both figures referring to the dried extract—compared to sterol levels of 1000 to 10,000 ppm in the dried plant material components. Surprisingly, it was thus discovered that beta-sitosterol, which has been described as having a hypoglycaemic action, is not the primary active substance. Rather the complete extract manufactured using the inventive process dictates biological activity.

The inventive extract preparations have a preferred plant material to extract ratio ranging from 1.5:1 to 20:1, preferably between 2:1 and 5:1.

The object of the disclosure is also a pharmaceutical product containing the inventive cactus pear extract formulations and the use of the inventive cactus pear extract formulations for manufacturing pharmaceutical products, nutritionally incomplete dietary foods for special medical purposes, dietary supplements and medical products (soluble fibre with *Opuntia* extracts, etc.) for the prevention and treatment of type 2 diabetes mellitus, metabolic syndrome and diseases correlated with it (diabetic vascular diseases, neuropathy, etc.) and for normalising blood glucose levels and favourable control of the blood lipid profile.

An important feature is that in diabetics, the hypoglycaemic properties do not cause actual hypoglycaemia, but lead to blood sugar being restored to normal levels only.

Surprisingly, in addition to the newly discovered hypoglycaemic effect of the inventive fruit skin extract, a significant increase in efficacy was discovered when this was combined with a cladode extract. Combining the two extracts demonstrates a synergistic effect of the individually efficacious individual extracts (example 3d). It is therefore possible either to extract two different plant components together or to produce two separate extract preparations which are then mixed.

The extract obtained can easily be converted into pharmaceutical preparations, including tablets, capsules, lozenges, gelatine soft capsules or liquid formulations such as drops, syrups, tinctures or mother tinctures. Further forms of administration are possible in foodstuffs such as drinks, yoghurt, bars, chewing gum, chewing pastilles, gelatine gums, etc.

Dosages from around 50 to 1,000 mg per dose, preferably 100-300 mg have proved particularly suitable, with a preferred daily intake of 1 to 3 doses.

The disclosure is elucidated further by means of the following examples.

Example 1a

Manufacture of a Thick Extract from Cactus Pear Fruit Skin:
14.5 kg of dried, chopped cactus pear fruit skin was mixed with water in a 1:14 ratio and percolated to completion at 80° C. in a Holstein-Kappert extractor. The eluate was drained from the plant material and residual plant material removed using a 250 µm filter bag. The percolate was evaporated in a plate evaporator. The resulting product was 14.5 kg of thick extract with a dry matter content of 58.3%.

Example 1b

Manufacture of a Thick Extract from Cactus Pear Cladodes:
12 kg of dried cactus pear cladodes chopped into 1 cm pieces was mixed with water in a 1:20 ratio and percolated to completion at 80° C. in a Holstein-Kappert extractor. The eluate was drained from the plant material and residual plant material removed using a 250 µm filter bag. The percolate was evaporated in a plate evaporator. The resulting product was 10.4 kg of thick extract with a dry matter content of 39.3%.

Example 1c

Manufacture of a Thick Extract from Cactus Pear Cladodes:
10 kg of dried cactus pear cladodes chopped into 1 cm pieces was mixed with ethanol 70% v/v in a 1:14 ratio and percolated to completion at 40° C. in a Holstein-Kappert extractor. The eluate was drained from the plant material and residual plant material removed using a 250 µm filter bag. The percolate was evaporated in a plate evaporator. The resulting product was 3.9 kg of thick extract with a dry matter content of 50.0%.

Example 1d

The thick extracts from examples 1a) and 1b) are mixed to homogeneity in a 1:1 ratio (calculated on the basis of the dry weight) using a stirrer.

Example 2a)

The mixture from example 1d) is autoclaved at 121° C. for 15 minutes.

Example 2b)

The mixture from example 1d) is subjected to enzyme treatment with a hemicellulase.

Example 2c)

The concentration of high molecular weight substances in the mixture from example 1d) is reduced using membrane filtration.

All the purification methods described in example 2 result in the hypoglycaemic effect remaining unchanged or becoming stronger.

Example 3a)

Manufacture of a Dry Extract from Cactus Pear Fruit Skin

Thick extract prepared as described in example 1a) is mixed with 30% microcrystalline cellulose (calculated on the basis of the dry weight) and gently dried in a vacuum at 50° C. After milling through a 0.5 mm sieve, a homogeneous, free-flowing powder is produced.

Example 3b)

Manufacture of a Dry Extract from Cactus Pear Cladodes

Thick extract prepared as described in example 1b) is mixed with 30% microcrystalline cellulose (calculated on the basis of the dry weight) and gently dried in a vacuum at 50° C. After milling through a 0.5 mm sieve, a homogeneous, free-flowing powder is produced.

Example 3c)

Manufacture of a Dry Extract from Cactus Pear Cladodes

Thick extract prepared as described in example 1c) is mixed with 30% microcrystalline cellulose (calculated on the basis of the dry weight) and gently dried in a vacuum at 50° C. After milling through a 0.5 mm sieve, a homogeneous, free-flowing powder is produced.

Example 3d)

Manufacture of a Dry Extract of Cactus Pear Cladodes and Cactus Pear Fruit Skin (50:50 m/m)

Thick extract prepared as described in example 1d) using water as the extraction medium is mixed with 30% microcrystalline cellulose (calculated on the basis of the dry weight) and gently dried in a vacuum at 50° C. After milling through a 0.5 mm sieve, a homogeneous, free-flowing powder is produced.

Example 3e)

Manufacture of a Dry Extract of Cactus Pear Cladodes and Cactus Pear Fruit Skin (50:50 m/m)

Thick extract prepared as described in example 1d) using water as the extraction medium is mixed with 30% microcrystalline cellulose (calculated on the basis of the dry weight) and gently spray-dried.

Example 3f)

Manufacture of a Dry Extract of Cactus Pear Cladodes and Cactus Pear Fruit Skin (50:50 m/m)

Thick extract prepared as described in example 1d) using water as the extraction medium is mixed with 30% microcrystalline cellulose (calculated on the basis of the dry weight) and lyophilised.

All drying processes described in example 3 are suitable for converting to a dry extract without resulting in a statistically significant reduction in the hypoglycaemic effect.

Example 4a)

Manufacture of a Water-Soluble Extract for Use in Drinks

After the addition of maltodextrin as a drying adjuvant in a ratio of 70% native extract:30% maltodextrin, the aqueous thick extract prepared as described in example 1d) was converted to a dry extract preparation by spray-drying. This extract preparation is fully water-soluble and can be added to drink concentrates, sodas, dietetic foods and dairy products in concentrations ranging from 1 to 10%. If, in place of maltodextrin, fructose or other, ideally sugar-free, water-soluble carriers with low glycaemic indices, such as hydrolysed proteins (Gelitasol, etc.), are used as drying adjuvants, these preparations can also be used in food products, nutritionally incomplete dietary foods for special medical purposes and drinks for diabetics.

Example 4b)

Pectin Lozenges 40 grams of standard commercial citrus pectin and 2 grams of trisodium citrate were mixed with 100 grams of Isomalt sugar substitute. This mixture was stirred into 200 ml water and, stirring continuously, heated until all the pectin had dissolved. A further 475 g Isomalt and 260 g fructose syrup were added and the mixture boiled until the dry matter content reached approx. 80%. 50 g of a cactus pear dry extract (example 3e) and colours and flavourings were now added. Approx. 17 ml of a 50% citric acid solution was added to achieve a pH of 3.4-3.5. The mixture was poured into moulds at a temperature of approx. 95° C. to obtain 2 g lozenges. 500 lozenges weighing 2 grams each can be manufactured in this way. One pectin lozenge contains approx. 100 mg of the cactus pear extract.

Example 4c)

Gum Arabic-Based Lozenges 15 kg of a 33% gum arabic, 5% sorbitol, 20% water and 42% maltitol solution was manufactured in a stirrer at 65° C.

500 grams of cactus pear dry extract (example 3f), plus flavourings and (if required) sweeteners to taste are stirred into this solution. After complete homogenisation, the mixture is poured into starch moulds. After drying at 50° C., the final weight of the lozenges is set to 2.0 g, each containing approx. 100 mg dry extract mixture and 3 mg lavender oil. The lozenges are separated from the starch, treated with a releasing agent and packaged. Approx. 5000 lozenges are obtained. One 2 g portion contains approx. 100 mg of the cactus pear extract.

Example 4d)

Chewing Gum 100 g chicle is powdered, mixed with 300 g Isomalt sugar substitute and heated in an evaporating dish until it softens. 5 g of cactus pear dry extract (example 3e)) is added and the mixture is mixed thoroughly, placed on a starched surface and kneaded to homogeneity. Flavourings may also be added during the previous step. The mixture is then rolled out into thin sheets and cut into flat sticks whilst still warm. The mixture is prevented from sticking to the surface by using a little starch powder. The chewing gum sticks should be 2 grams in weight and contain approx. 100 mg of the cactus pear extract.

Example 4e)

Manufacture of a Pharmaceutical Tablet Composition

The inventive extract prepared as described in example 3d) is directly pressed into tablets using the following recipe.

300 mg inventive cactus pear dry extract 160 mg microcrystalline cellulose 25 mg sodium carboxymethylcellulose 10 mg highly dispersed silicon dioxide 5 mg magnesium stearate Example 4f)

Manufacture of a Pharmaceutical Hard Gelatine Capsule Composition

The inventive extract under example 3d) is directly filled into capsules using the following recipe.
200 mg extract per capsule
50 mg microcrystalline cellulose
2 mg highly dispersed silicon dioxide Example 5

Study on the Hypoglycaemic Effect in an Animal Model—Oral Glucose Tolerance Test (oGTT)

A standard means of testing extracts or novel chemical compounds for effects on blood sugar levels is the oGTT (Verspohl, 2002). This involves administering the extract, a blind control or a known anti-diabetic to different groups of a rat population and administering an intraperitoneal dose of glucose to a sub-group of each group. The extracts were administered 30 minutes before the glucose. Blood samples were taken sublingually 0, 15, 30, 60 and 120 minutes after glucose administration or at 0, 30, 60, 120 and 180 minutes for baseline blood sugar levels. The sampling schedule described served both to track the effect of the extracts on baseline blood sugar levels over a longer period and to track the effect on blood sugar levels following a glucose load.

All of the tested extracts, the blind control and the glibenclamide reference oral anti-diabetic contained propylene glycol as a solubilising agent and were administered orally via a feeding tube.

Experimental Animals

Male non-fasted Wistar rats weighing between 250 and 300 g obtained from Harlan (Indianapolis, Ind., U.S.A).

The non-fasted state was selected to ensure a more natural physiology, but also resulted in a greater degree of variation in natural blood glucose levels. The rats were kept in pairs in cages at 20±1° C. in a 12-hour light-dark cycle. Water and feed pellets were freely available. Groups of 6 rats were randomly assigned to each of the 12 different test groups. All experiments were carried out in a quiet room between 9 am and 2 μm. The experiments were carried out and the animals kept in accordance with the principles and guidelines of the Institutional Animal Care and Use Committee (IACUC) (University of Florida, Gainesville, USA).

Materials

Glibenclamide (glyburide, Sigma-Aldrich, St. Louis, U.S.A) was used as a known reference anti-diabetic at a dosage of 18 mg/kg as described in the literature (Subash Babu et al., 2007; Verspohl et al., 2005). It was diluted with deionised water to 18 mg/5 ml at a propylene glycol concentration of 0.5%.

The test extracts were suspended in 5 ml deionised water containing 0.5% propylene glycol. All test solutions were freshly prepared daily. All animals were delivered to the test area at least 30 minutes before testing and remained in the test area throughout the test. The glucose (Sigma-Aldrich) was dissolved in a 0.9% saline solution to a concentration of 2 g/5 ml (with the aid of an ultrasonic device) and administered intraperitoneally 30 minutes after administration of the test solution.

Blood Glucose Determination

Following halothane anaesthesia, at the scheduled time points blood was taken from the sublingual vein, heparinised and stored at 4° C.

The samples were centrifuged at 8600 U/min for 10 minutes. The plasma supernatant was then analysed using an autoanalyser (Merck, Darmstadt). Analytic plasma controls and blanks were used to ensure precise results within the specified range.

FIG. 1 shows the hypoglycaemic effect following administration of two dry extracts of cactus pear cladodes compared to NaCl solution (control) in the oGTT model in rats (n=6). A measurable reduction in blood glucose compared to untreated animals was observed. With a reduction of up to 20%, extract 3b) was significantly more potent than extract 3c (−3%).

Figure 2:
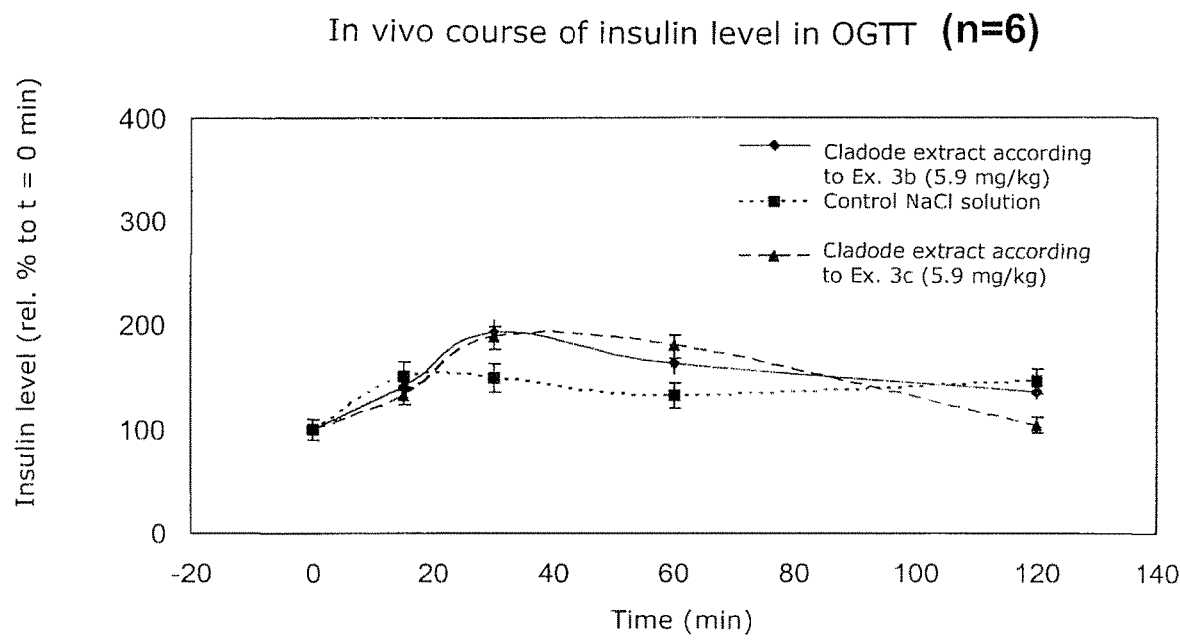
FIG. 2 shows insulin release

FIG. 2 shows the insulin level curve following administration of two dry extracts of cactus pear cladodes compared to NaCl solution (control) in the oGTT model in rats (n=6). A measurable increase in insulin release (+20%) compared to untreated animals was observed.

Statistics and Calculations

Concentrations and kinetic data were analysed in Graphpad 4.0 (San Diego, USA) using one-way variance analysis (ANOVA) and the Newman-Keuls multiple comparison test. The area under the curve (AUC) was determined using the trapezoidal method without extrapolation beyond the final sampling point.

Results

The reference substance, glibenclamide, confirmed the suitability of the test model for measuring a hypoglycaemic effect compared to the control group. Extracts of both cactus pear cladodes and cactus pear fruit skin also exhibited significant hypoglycaemic effects. By contrast, powdered plant material (cladodes) showed no statistically significant effect even in significantly higher doses. Surprisingly, a mixture of different cactus pear plant components, a 50:50 mixture of cladodes and fruit skin tested here, showed a synergistic effect compared to the individual extracts (see FIG. 3). This suggests differing modes of action.

Figure 3:
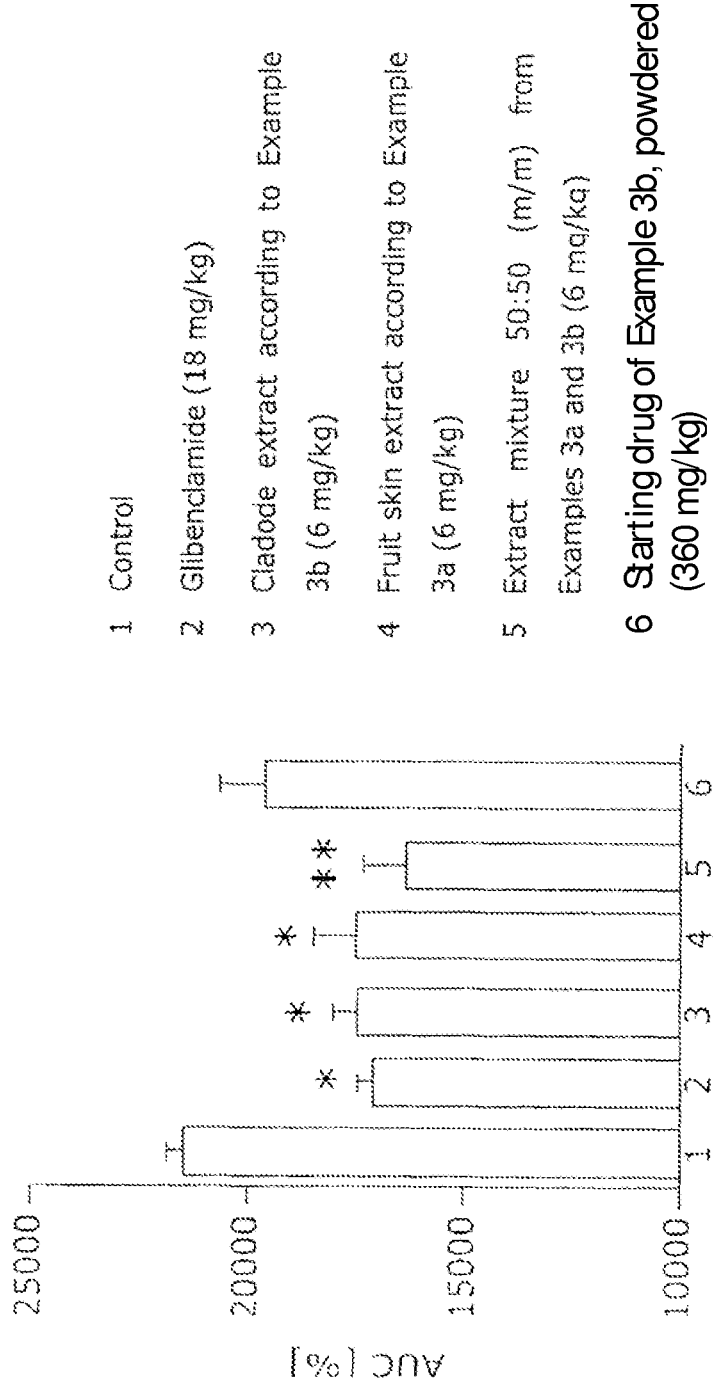
FIG. 3 shows the in vivo oral glucose tolerance test for extracts obtained from cladodes, extracts obtained from fruits and a 50:50 w/w mixture thereof manufactured in accordance with the inventive method compared to a control/glibenclamide.

FIG. 3 shows the effect of glibenclamide and the inventive extracts in the oGTT (oral glucose tolerance test), expressed as percent AUC, for n=5-6 per test group; level of significance vs. control: * $p<0.05$, ** $p<0.01$.

The invention claimed is:

1. An *Opuntia ficus-indica* extract preparation for decreasing blood sugar and increasing insulin comprising:
  (i) an effective amount of an *Opuntia ficus-indica* extract formulation containing less than 100 ppm of sterols and less than 10 ppm of beta sitosterol, wherein the *Opuntia ficus-indica* extract formulation consists of: i.) an extract of dried fruit skins of *Opuntia ficus-indica*, and ii.) an extract of dried cladodes of *Opuntia ficus-indica* in a ratio of 1:1, and wherein the *Opuntia ficus-indica* extract formulation is obtained by:
    (a) treating dried fruit skins of *Opuntia ficus-indica* with a first extractant consisting of water, wherein the first extractant separates the dried fruit skins of *Opuntia ficus-indica* into fruit skin plant material that includes first constituents that have been solubilized by the first extractant and fruit skin plant residue that has not been solubilized by the first extractant;
    (b) removing at least a portion of the first extractant to produce an *Opuntia ficus-indica* fruit skin extract;
    (c) treating dried cladodes of *Opuntia ficus-indica* with a second extractant consisting of water, wherein the second extractant separates the dried cladodes of *Opuntia ficus-indica* into cladode plant material containing second constituents that have been solubilized by the second extractant and cladode plant residue that has not been solubilized by the second extractant;

(d) removing at least a portion of the second extractant to produce an *Opuntia ficus-indica* cladode extract; and (e) mixing the *Opuntia ficus-indica* fruit skin extract produced in step b) with the *Opuntia ficus-indica* cladode extract produced in step d) to provide the *Opuntia ficus-indica* extract formulation; and (ii) a carrier selected from microcrystalline cellulose and hydrolyzed protein.

2. The *Opuntia ficus-indica* extract preparation of claim 1, wherein the *Opuntia ficus-indica* cladode extract formulation is dried together with the carrier.

3. The *Opuntia ficus-indica* extract preparation of claim 1, wherein the water in the extraction of *Opuntia ficus-indica* fruit skin is heated to a temperature of about 50-90° Celsius and the water in the extraction of *Opuntia ficus-indica* cladode is heated to a temperature of about 50-90° Celsius.

4. The *Opuntia ficus-indica* extract preparation of claim 1, wherein the extraction of *Opuntia ficus-indica* fruit skin and the extraction of *Opuntia ficus-indica* cladode is carried out over a range of from 2 to 6 hours.

5. The *Opuntia ficus-indica* extract preparation of claim 1, wherein the *Opuntia ficus-indica* extract preparation is an oral dosage form that is selected from the group consisting of a free-flowing powder, a tablet, a hard capsule, a soft capsule, a lozenge, a drop and a syrup.

6. The *Opuntia ficus-indica* extract preparation of claim 1, further comprising a step of performing enzyme treatment on at least one of the *Opuntia ficus-indica* fruit skin extract and the *Opuntia ficus-indica* cladode extract.

7. The *Opuntia ficus-indica* extract preparation of claim 1, further comprising a step of performing membrane filtration on at least one of the *Opuntia ficus-indica* fruit skin extract and the *Opuntia ficus-indica* cladode extract.

8. The *Opuntia ficus*-indicia extract preparation of claim 1, wherein the carrier is present in the *Opuntia ficus*-indicia extract preparation in an amount of about 30% by weight and the *Opuntia ficus-indica* extract formulation is present in the *Opuntia ficus*-indicia extract preparation in an amount of about 70% by weight.

9. A foodstuff, dietetic foodstuff, food supplement or medicament comprising the *Opuntia ficus-indica* extract preparation according to claim 1.

* * * * *